(12) United States Patent
McChesney et al.

(10) Patent No.: US 11,530,596 B2
(45) Date of Patent: Dec. 20, 2022

(54) FLUID FLOW CONTROL DEVICES AND DOWNHOLE FLOATS

(71) Applicant: Halliburton Energy Services, Inc., Houston, TX (US)

(72) Inventors: Ryan Wesley McChesney, Prosper, TX (US); Stephen Michael Greci, Little Elm, TX (US); Richard Decena Ornelaz, Frisco, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 16 days.

(21) Appl. No.: 17/130,859

(22) Filed: Dec. 22, 2020

(65) Prior Publication Data

US 2022/0195837 A1 Jun. 23, 2022

(51) Int. Cl.
*E21B 34/06* (2006.01)

(52) U.S. Cl.
CPC .................... *E21B 34/06* (2013.01)

(58) Field of Classification Search
CPC .......... E21B 34/06; E21B 34/08; E21B 43/12
See application file for complete search history.

(56) References Cited

U.S. PATENT DOCUMENTS

| 2013/0092393 A1* | 4/2013 | Dykstra | E21B 43/12 166/373 |
| 2015/0000751 A1* | 1/2015 | Nicholson | F16K 31/20 137/434 |
| 2020/0291745 A1 | 9/2020 | Greci et al. | |
| 2020/0308927 A1 | 10/2020 | Fripp et al. | |

FOREIGN PATENT DOCUMENTS

| CN | 103732854 A | 4/2014 |
| WO | 2019078821 | 4/2019 |
| WO | 2019135814 | 7/2019 |
| WO | 2020117230 A1 | 6/2020 |

OTHER PUBLICATIONS

International Search Report and Written Opinion date dated Sep. 10, 2021; International PCT Application No. PCT/US2020/066863.

* cited by examiner

*Primary Examiner* — Matthew R Buck
(74) *Attorney, Agent, or Firm* — McGuireWoods LLP

(57) ABSTRACT

Fluid flow control devices and downhole floats are presented. A fluid flow control device includes a port and a rotatable component that rotates about an axis in response to fluid flow from the port. The fluid flow control device also includes an outlet port that provides a fluid passageway out of the rotatable component. The fluid flow control device further includes a float positioned within the rotatable component, where the float is shiftable from an open position to a closed position, and where the float restricts fluid flow through the outlet port while the float is in the closed position.

15 Claims, 7 Drawing Sheets

FLUID FLOW CONTROL DEVICES AND DOWNHOLE FLOATS

BACKGROUND

The present disclosure relates generally to fluid flow control devices and downhole floats.

Wellbores are sometimes drilled from the surface of a wellsite several hundred to several thousand feet downhole to reach hydrocarbon resources. During certain well operations, such as production operations, certain fluids, such as fluids of hydrocarbon resources, are extracted from the formation, where fluids of hydrocarbon resources flow into one or more sections of a conveyance such as a section of a production tubing, and through the production tubing, uphole to the surface. During production operations, other types of fluids, such as water, sometimes also flow into the section of production tubing while fluids of hydrocarbon resources are being extracted.

BRIEF DESCRIPTION OF THE DRAWINGS

Illustrative embodiments of the present disclosure are described in detail below with reference to the attached drawing figures, which are incorporated by reference herein, and wherein.

Figure 1:
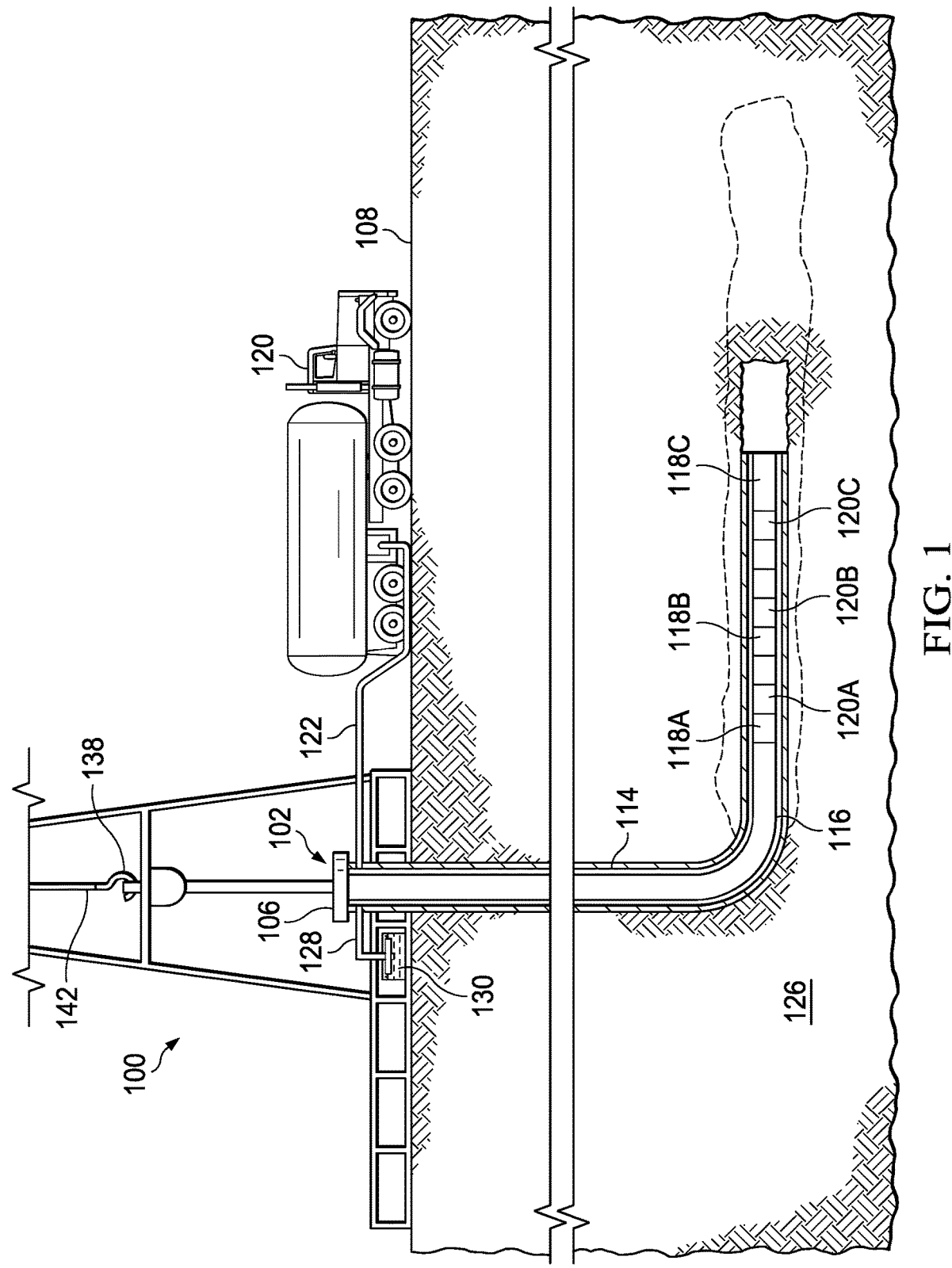
FIG. 1 is a schematic, side view of a well environment in which three inflow flow control devices are deployed in a wellbore.

The illustrated figures are only exemplary and are not intended to assert or imply any limitation with regard to the environment, architecture, design, or process in which different embodiments may be implemented.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments is defined only by the appended claims.

The present disclosure relates to fluid flow control devices and downhole floats. The fluid flow control device includes a port, such as an inlet port, and a rotatable component that rotates about an axis in response to fluid flow from the port. In some embodiments, force applied by fluids flowing through the inlet port during certain operations, such as drilling operations, fracturing operations, and production operations, rotate the rotatable component. The fluid flow control device also includes an outlet port that provides a fluid passageway out of the rotatable component.

The fluid flow control device also includes a float that is positioned within the rotatable component. The float is shiftable from an open position to a closed position that restricts fluid flow through the outlet port while the float is in the closed position, and from the closed position to the open position to permit fluid flow through the outlet port. As referred to herein, an open position is a position of the float where the float does not restrict fluid flow through the outlet port, whereas a closed position is a position of the float where the float restricts fluid flow through the outlet port. In some embodiments, the float shifts radially inwards towards the outlet port to move from an open position to a closed position, and shifts radially outwards away from the outlet port to move from the closed position to the open position. As referred to herein, radially inwards means shifting radially towards the center, such as the central axis of a rotatable component, whereas radially outwards means shifting away from the center, such as away from the central axis of the rotatable component and towards the parameters of the rotatable component. In some embodiments, the float shifts circumferentially (such as circumferentially about a flow pathway or a port) from a first position to a second position to move from an open position to a closed position, and shifts from the second position to the first position to move from the closed position to the open position. In some embodiments, the float opens to permit certain types of fluids having densities that are less than a threshold density (such as oil and other types of hydrocarbon resources) to flow through the outlet port, and restricts other types of fluids having densities greater than or equal to the threshold density (such as water and drilling fluids) from flowing through the outlet port.

In some embodiments, the float has a cavity disposed within the float. In one or more of such embodiments, the cavity is at least partially filled with a material or a foam having a density such that the net density of the float and the material or the fluid and the foam, respectively, is less than the density of an undesired fluid, such as water, and is greater than the density of a desired fluid, such as oil. In one or more of such embodiments, one or more weights are disposed in the cavity. In one or more of such embodiments, the weights are movable within the cavity, and movement of the weights from one position to another position shifts the float from an open position to a closed position. In one or more of such embodiments, movement of the weights also shifts the float's center of gravity. In some embodiments, the float includes one or more inserts that are formed along a portion of the float. In one or more of such embodiments, weights are disposed in different inserts based on a desired density and center of gravity of the float. In one or more of such embodiments, weights are moved to different inserts to adjust the density and center of gravity of the float. In some embodiments, the float is coupled to or is positioned near a spring component of the fluid flow control device. In one or more of such embodiments, centrifugal force generated by the rotatable component spinning shifts the float radially outwards towards the parameter of the rotatable components to an open position. In some embodiments, where the rotatable component is partially filled with certain undesired fluids (e.g., water) that have a first density, the undesirable fluids exert a force on the float that shifts the float radially outwards towards the parameter. As the float shifts radially outwards, the float also compresses the spring. As the rotatable component spins below a threshold speed or accelerates below a threshold rate, force generated by the compressed spring returning to a natural state exceeds the centrifugal force, and the spring shifts the float radially inwards and to the closed position. Similarly, where the rotatable component is partially filled with certain desired fluids (e.g., oil) that have a second density that is less than the first density, force generated by the compressed spring returning to a natural state exceeds the force exerted by the desired fluids and the spring shifts the float radially inwards and to the closed position. Additional descriptions of inflow control devices, fluid flow control devices, and downhole floats are provided in the paragraphs below and are illustrated in FIGS. 1-9.

Turning now to the figures, FIG. 1 is a schematic, side view of a well environment 100 in which inflow control devices 120A-120C are deployed in a wellbore 114. As shown in FIG. 1, wellbore 114 extends from surface 108 of well 102 to or through formation 126. A hook 138, a cable 142, traveling block (not shown), and hoist (not shown) are provided to lower conveyance 116 into well 102. As referred to herein, conveyance 116 is any piping, tubular, or fluid conduit including, but not limited to, drill pipe, production tubing, casing, coiled tubing, and any combination thereof. Conveyance 116 provides a conduit for fluids extracted from formation 126 to travel to surface 108. In some embodiments, conveyance 116 additionally provides a conduit for fluids to be conveyed downhole and injected into formation 126, such as in an injection operation. In some embodiments, conveyance 116 is coupled to a production tubing that is arranged within a horizontal section of well 102. In the embodiment of FIG. 1, conveyance 116 and the production tubing are represented by the same tubing.

At wellhead 106, an inlet conduit 122 is coupled to a fluid source 120 to provide fluids through conveyance 116 downhole. For example, drilling fluids, fracturing fluids, and injection fluids are pumped downhole during drilling operations, hydraulic fracturing operations, and injection operations, respectively. In the embodiment of FIG. 1, fluids are circulated into well 102 through conveyance 116 and back toward surface 108. To that end, a diverter or an outlet conduit 128 may be connected to a container 130 at the wellhead 106 to provide a fluid return flow path from wellbore 114. Conveyance 116 and outlet conduit 128 also form fluid passageways for fluids, such as hydrocarbon resources to flow uphole during production operations.

In the embodiment of FIG. 1, conveyance 116 includes production tubular sections 118A-118C at different production intervals adjacent to formation 126. In some embodiments, packers (now shown) are positioned on the left and right sides of production tubular sections 118A-118C to define production intervals and provide fluid seals between the respective production tubular section 118A, 118B, or 118C, and the wall of wellbore 114. Production tubular sections 118A-118C include inflow control devices 120A-120C (ICDs). An inflow control device controls the volume or composition of the fluid flowing from a production interval into a production tubular section, e.g., 118A. For example, a production interval defined by production tubular section 118A produces more than one type of fluid component, such as a mixture of water, steam, carbon dioxide, and natural gas. Inflow control device 120A, which is fluidly coupled to production tubular section 118A, reduces or restricts the flow of fluid into the production tubular section 118A when the production interval is producing a higher proportion of an undesirable fluid component, such as water, which permits the other production intervals that are producing a higher proportion of a desired fluid component (e.g., oil) to contribute more to the production fluid at surface 108 of well 102, so that the production fluid has a higher proportion of the desired fluid component. In some embodiments, inflow control devices 120A-120C are an autonomous inflow control devices (AICD) that permits or restricts fluid flow into the production tubular sections 118A-118C based on fluid density, without requiring signals from the well's surface by the well operator.

Although the foregoing paragraphs describe utilizing inflow control devices 120A-120C during production, in some embodiments, inflow control devices 120A-120C are also utilized during other types of well operations to control fluid flow through conveyance 116. Further, although FIG. 1 depicts each production tubular section 118A-118C having an inflow control device 120A-120C, in some embodiments, not every production tubular section 118A-118C has an inflow control device 120A-120C. In some embodiments, production tubular sections 118A-118C (and inflow control devices 120A-120C) are located in a substantially vertical section additionally or alternatively to the substantially horizontal section of well 102. Further, any number of production tubular sections 118A-118C with inflow control devices 120A-120C, including one, are deployable well 102. In some embodiments, production tubular sections 118A-118C with inflow control devices 120A-120C are disposed in simpler wellbores, such as wellbores having only a substantially vertical section. In some embodiments, inflow control devices 120A-120C are disposed in cased wells or in open-hole environments.

Figure 2:
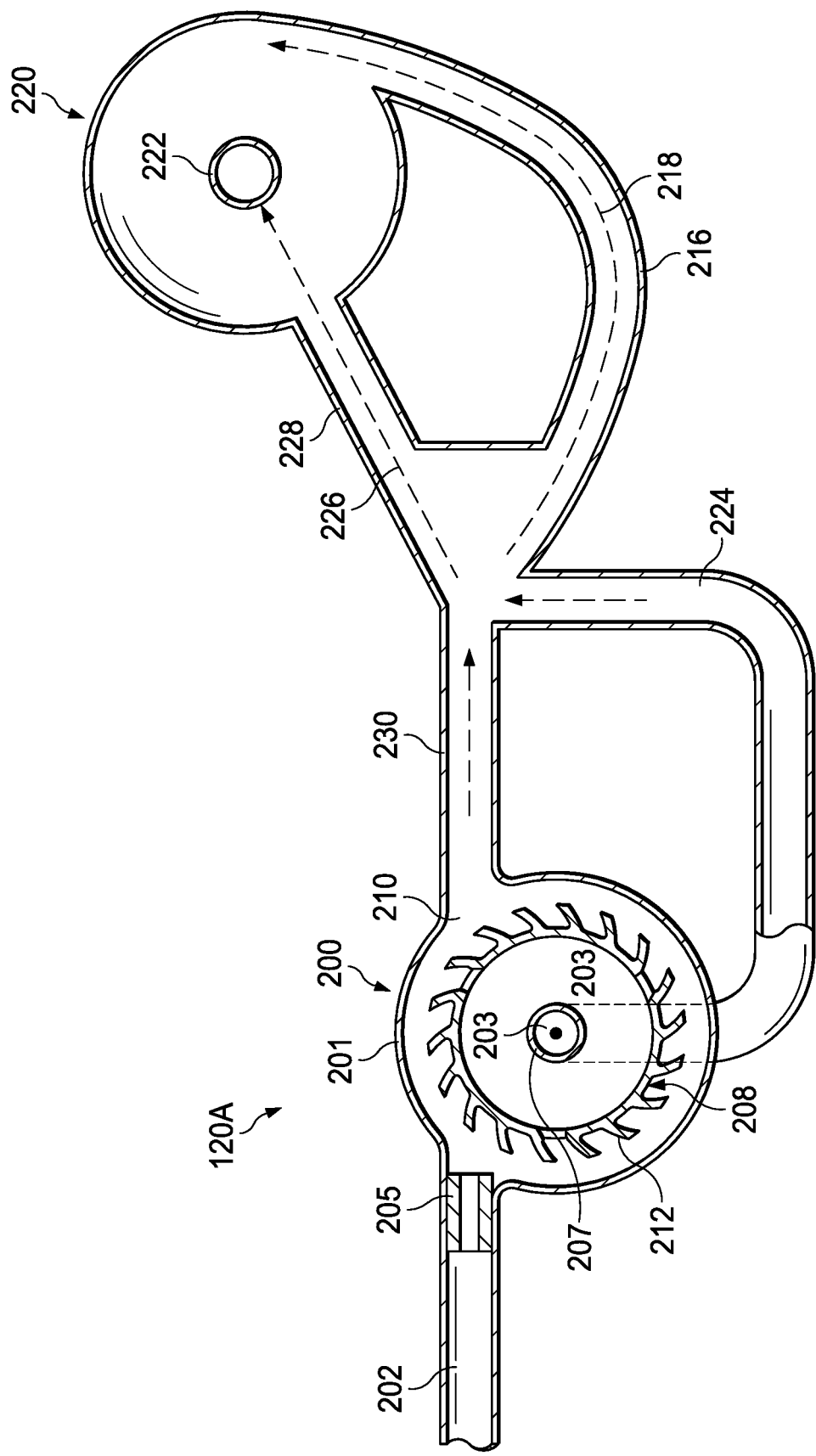
FIG. 2 is a cross-sectional view of a flow control device of FIG. 1.

FIG. 2 is a cross-sectional view of inflow control device 120A of FIG. 1. In the embodiments described herein, inflow control device 120A includes an inflow tubular 200 of a well tool coupled to a fluid flow control device 202. Although the word "tubular" is used to refer to certain components in the present disclosure, those components have any suitable shape, including a non-tubular shape. Inflow tubular 200 provides fluid to fluid flow control device 202. In some embodiments, fluid is provided from a production interval in a well system or from another location. In the embodiment of FIG. 2, inflow tubular 200 terminates at an inlet port 205 that provides a fluid communication pathway into fluid flow control device 202. In some embodiments, inlet port 205 is an opening in a housing 201 of fluid flow control device 202.

A first fluid portion flows from inlet port 205 toward a bypass port 210. The first fluid portion pushes against fins 212 extending outwardly from a rotatable component 208 to rotate rotatable component 208 to rotate about an axis, such as a central axis 203. Rotation of rotatable component 208 about axis 203 generates a force on a float (not shown) positioned within rotatable component 208. After passing by rotatable component 208, the first fluid portion exits fluid flow control device 202 via bypass port 210. From bypass port 210, the first fluid portion flows through a bypass tubular 230 to a tangential tubular 216. The first fluid portion flows through tangential tubular 216, as shown by dashed arrow 218, into a vortex valve 220. In the embodiment of FIG. 2, the first fluid portion to spin around an outer perimeter of vortex valve 220 at least partially due to the angle at which the first fluid portion enters vortex valve 220. Forces act on the first fluid portion, eventually causing the first fluid portion to flow into a central port 222 of vortex valve 220. The first fluid portion then flows from central port 222 elsewhere, such as to a well surface as production fluid.

At the same time, a second fluid portion from inlet port 205 flows into rotatable component 208 via holes in rotatable component 208 (e.g., holes between fins 212 of rotatable component 208). If the density of the second fluid portion is high, the float moves to a closed position, which prevents the second fluid portion from flowing to an outlet port 207, and instead cause the second fluid portion to flow out bypass port 210. If the density of the second fluid portion is low (e.g., if the second fluid portion is mostly oil or gas), then the float moves to an open position that allows the second fluid portion to flow out the outlet port 207 and into a control tubular 224. In this manner, fluid flow control device 202 autonomously directs fluids through different pathways based on the densities of the fluids. The control tubular 224 directs the second fluid portion, along with the first fluid portion, toward central port 222 of vortex valve 220 via a more direct fluid pathway, as shown by dashed arrow 226 and defined by tubular 228. The more direct fluid pathway to central port 222 allows the second fluid portion to more directly flow into central port 222, without first spinning around the outer perimeter of vortex valve 220. If the bulk of the fluid enters vortex valve 220 along the pathway defined by dashed arrow 218, then the fluid will tend to spin before exiting through central port 222 and will have a high fluid resistance. If the bulk of the fluid enters vortex valve 220 along the pathway defined by dashed arrow 226, then the fluid will tend to exit through central port 222 without spinning and will have minimal flow resistance.

In some embodiments, the above-mentioned concepts are enhanced by the rotation of rotatable component 208. Typically, the buoyancy force generated by the float is small because the difference in density between the lower-density fluid and the higher-density fluid is generally small, and there is only a small amount (e.g., 5 milli-Newtons) of gravitational force acting on this difference in density. This makes fluid flow control device 202 sensitive to orientation, which causes the float to get stuck in the open position or the closed position. However, rotation of rotatable component 208 creates a force (e.g., a centripetal force or a centrifugal force) on the float. The force acts as artificial gravity that is much higher than the small gravitational force naturally acting on the difference in density. This allows fluid flow control device 202 to more reliably toggle between the open and closed positions based on the density of the fluid. This also makes fluid flow control device 202 perform in a manner that is insensitive to orientation, because the force generated by rotatable component 208 is much larger than the naturally occurring gravitational force.

In some embodiments, fluid flow control device 202 directs a fluid along the more direct pathway shown by dashed arrow 226 or along the tangential pathway shown by dashed arrow 218. In one or more of such embodiments, whether fluid flow control device 202 directs the fluid along the pathway shown by dashed arrow 226 or the dashed arrow 218 depends on the composition of the fluid. Directing the fluid in this manner causes the fluid resistance in vortex valve 220 to change based on the composition of the fluid.

In some embodiments, fluid flow control device 202 is compatible with any type of valve. For example, although FIG. 2 includes a vortex valve 220, in other embodiments, vortex valve 220 is replaced with other types of fluidic valves, including valves that have a moveable valve-element, such as a rate controlled production valve. Further, in some embodiments, fluid control device 202 operates as a pressure sensing module in a valve.

Figure 3:
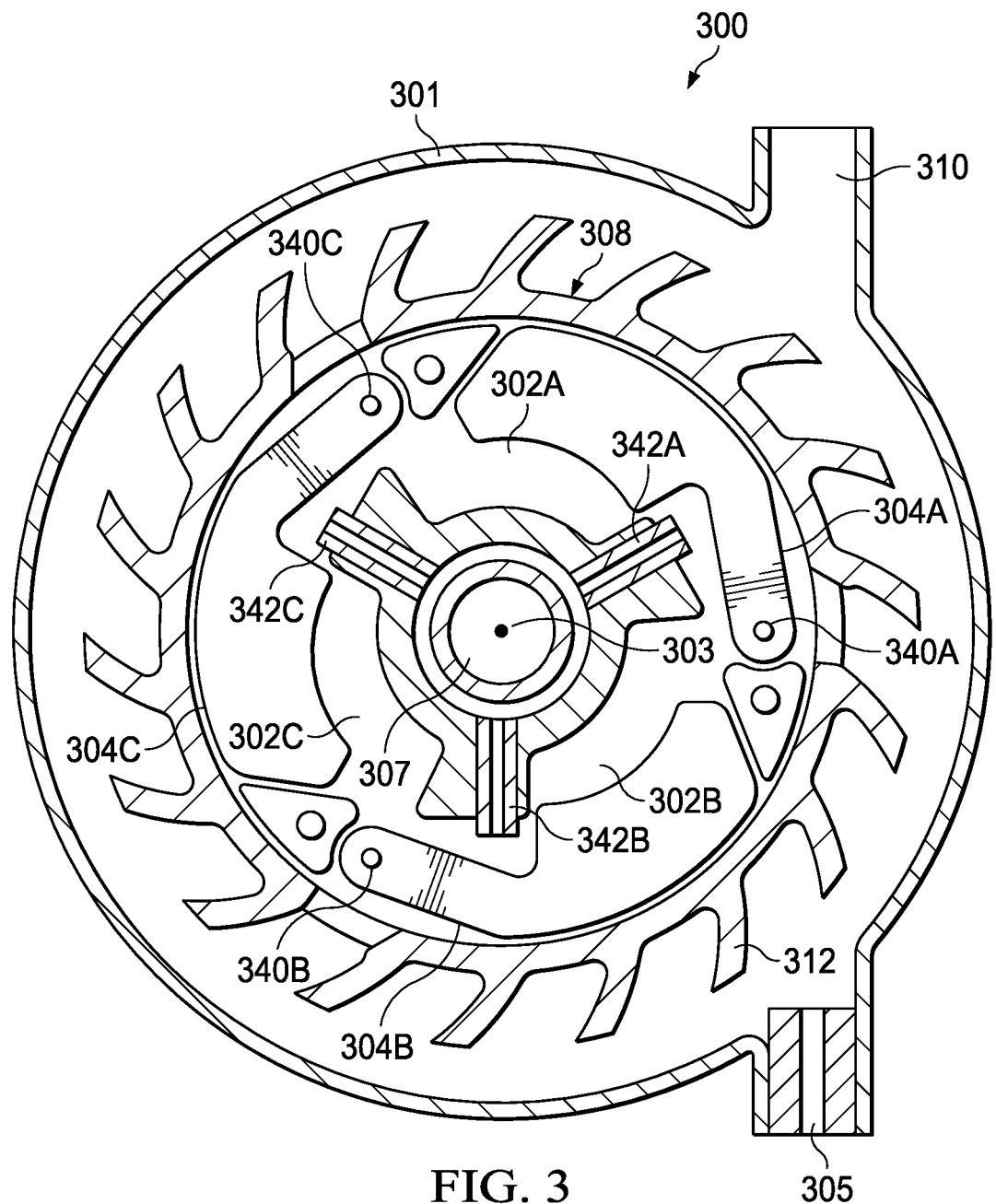
FIG. 3 is a cross-sectional view of a portion of a fluid flow control device similar to the fluid flow control device of FIG. 2.

FIG. 3 is a cross-sectional view of a fluid flow control device 300 similar to fluid flow control device 200 of FIG. 2. With reference now to FIG. 3, fluid flow control device 300 includes a rotatable component 308 positioned within a housing 301 of fluid flow control device 300. Fluid flow control device 300 also includes an inlet port 305 that provides a fluid passage for fluids such as, but not limited to, hydrocarbon resources, wellbore fluids, water, and other types of fluids to flow into housing 301. Fluid control device 300 also includes an outlet port 310 that provides a fluid flow path for fluids to flow out of fluid flow control device 300, such as to vortex valve 220 of FIG. 2. Some of the fluids that flow into housing 301 also come into contact with rotatable component 308, where force generated by fluids flowing onto rotatable component 308 rotates rotatable component 308 about axis 303. In some embodiments, fluids flowing through inlet port 305 push against fins, including fin 312, which are coupled to rotatable component 308, where the force of the fluids against the fins rotates rotatable component 308 about axis 303. Three floats 304A-304C are positioned within the rotatable component 308 and are connected to the rotatable component 308 by hinges 340A-340C, respectively, where each hinge 340A, 340B, and 340C provides for movement of a respective float 304A, 304B, and 304C relative to rotatable component 308 between the open and closed positions. In some embodiments, movements of each float 304A, 304B, and 304C between the open and the closed positions are based on fluid densities of fluids in rotatable component 308.

In some embodiments, movement of floats 304A-304C back and forth between the open and closed positions is accomplished by hinging each respective float 304A, 304B, or 304C on its hinge 340A, 340B, or 340C. In some embodiments, each hinge 340A, 340B, and 340C includes a pivot rod (not shown) mounted to rotatable component 308 and passing at least partially through float 304A, 304B, and 304C, respectively. In some embodiments, in lieu of the pivot rod mounted to rotatable component 308, each float 304A, 304B, and 304C has bump extensions that fit into recesses of rotatable component 308 for use as a hinge. In some embodiments, floats 304A-304C are configured to move back and forth from the open and closed positions in response to changes in the average density of fluids, including mixtures of water, hydrocarbon gas, and/or hydrocarbon liquids, introduced at inlet port 305. For example, floats 304A-304C are movable from the open position to the closed position in response to the fluid from inlet port 305 being predominantly water, wherein the float component is movable from the closed position to the open position in response to the fluid from the inlet port 305 being predominantly a hydrocarbon.

In the embodiment of FIG. 3, rotatable component 308 includes three fluid pathways 342A-342C that provide fluid communication between inlet port 305 and an outlet port 307. Further, each fluid pathway 342A, 342B, and 342C is fluidly connected to a chamber 302A, 302B, and 302C, respectively. Moreover, each float 304A, 304B, and 304C is disposed in a chamber 302A, 302B, and 302C, respectively, such that shifting a float 304A, 304B, or 304C from an open position to a closed position restricts fluid flow through a corresponding fluid pathway 342A, 342B, or 342C, respectively, whereas shifting float 304A, 304B, or 304C from the closed position to the open position permits fluid flow through corresponding fluid pathway 342A, 342B, or 342C. In some embodiments, float 304A, 304B, or 304C permits or restricts fluid flow through fluid pathway 342A, 342B, or 342C, respectively, based on the density of the fluid in chamber 302A, 302B, or 302C, respectively. Although FIG. 3 illustrates three floats 304A-304C positioned in three chambers 302A-202C, respectively, in some embodiments, a different number of floats positioned in a different number of chambers are placed in rotatable component 308. Further, although FIG. 3 illustrates three fluid pathways 342A-342C, in some embodiments, rotatable component 308 includes a different number of fluid pathways that fluidly connect inlet port 305 to outlet port 307. Further, although FIG. 3 illustrates three floats 304A-304C positioned in three chambers 302A-202C, respectively, in some embodiments, a different number of floats positioned in a different number of chambers are placed in rotatable component 308. Further, although FIG. 3 illustrates three fluid pathways 342A-342C, in some embodiments, rotatable component 308 includes a different number of fluid pathways that fluidly connect inlet port 305 to outlet port 307.

Figure 4:
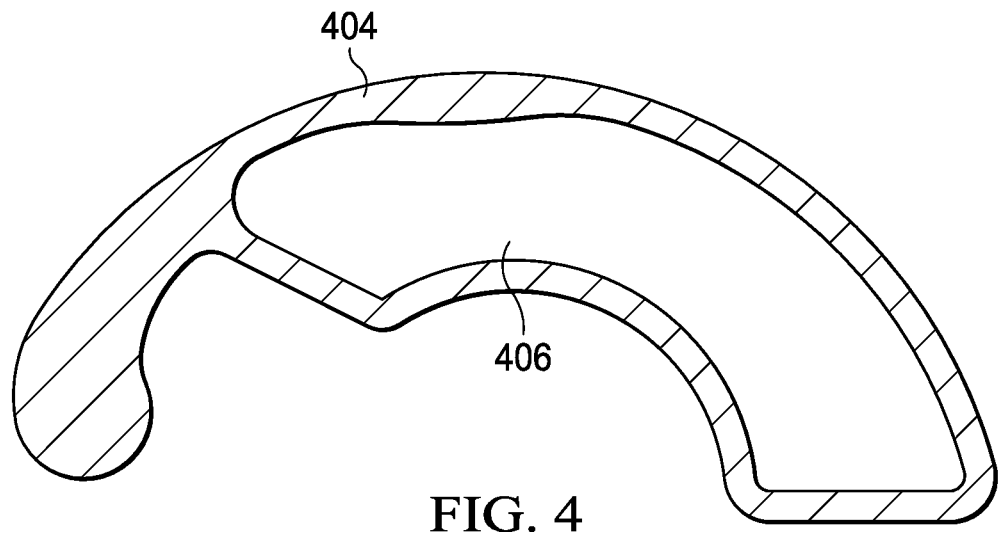
FIG. 4 is a cross-sectional view of a type of float of the fluid flow control device of FIG. 3.

FIG. 4 is a cross-sectional view of a type of float 404 of fluid flow control device 300 of FIG. 3. In the embodiment of FIG. 4, float 404 has an impermeable exterior and an internal cavity 406. In some embodiments, the exterior is formed from a metal, a metallic alloy, polyether ether ketone, a plastic, a thermoplastic, an epoxy, or a composite. In some embodiments, internal cavity 406 is a hollow void formed within float 404. In some embodiments, internal cavity 406 is partially filled with a lattice structure to provide support for hydrostatic pressure. In some embodiments, internal cavity 406 is partially filled with a solid, liquid, or gas having a specific density such that the net density of float 404 is below the density of undesired fluids (e.g., water) and is above the density of desired fluids (e.g., oil). In some embodiments, float 404 is manufactured from a casting process. In some embodiments, float 404 is 3D printed. In some embodiments, pieces of float 404 are welded or glued together to form float 404.

Figure 5:
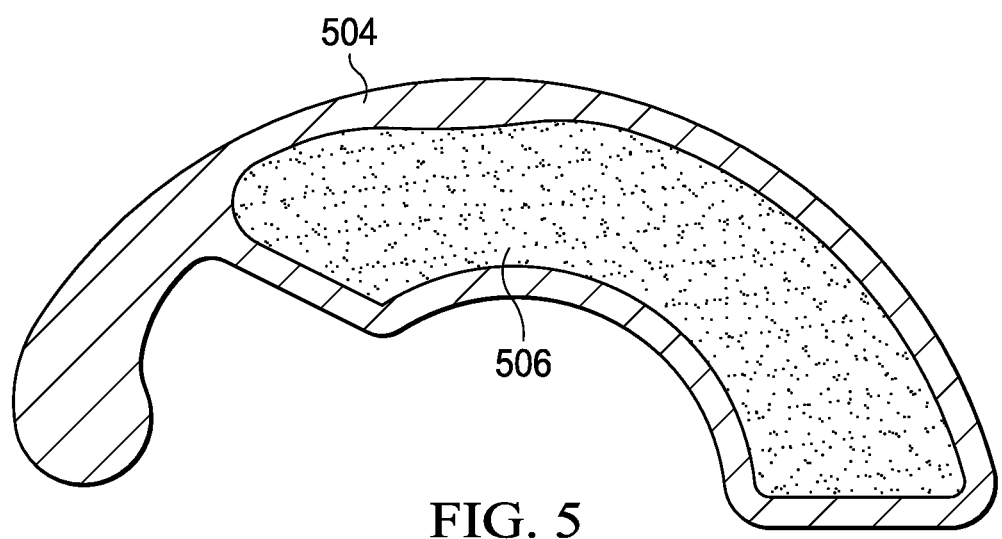
FIG. 5 is a cross-sectional view of another type of float of the fluid flow control device of FIG. 3.

FIG. 5 is a cross-sectional view of another type of float 504 of fluid flow control device 300 of FIG. 3. In the embodiment of FIG. 5, a foam 506 is encapsulated inside an exterior shell, and has a density such that the float and the foam have a net density that is above a density of a desired fluid and is below a density of an undesired fluid. Further, foam 506. In some embodiments, the exterior shell is formed from polyether ether ketone, polyphenylene sulfide, thermoplastic, epoxy, or a composite. In some embodiments, ether ketone, polyphenylene sulfide, or a composite is injection molded around foam 506 to encapsulate foam 506. In some embodiments, an impermeable exterior shell is formed around foam 506 to prevent fluids from penetrating the shell.

Figure 6:
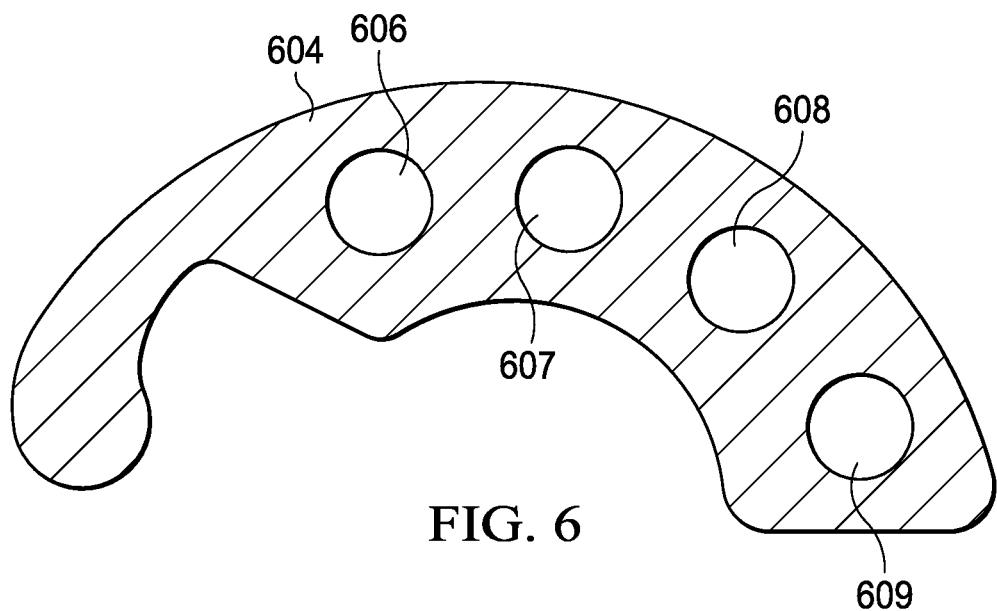
FIG. 6 is a cross-sectional view of another type of float of the fluid flow control device of FIG. 3.

FIG. 6 is a cross-sectional view of another type of float 604 of fluid flow control device 300 of FIG. 3. In the embodiment of FIG. 6, float 604 has four inserts 606-609 disposed inside float 604. In the embodiment of FIG. 6, each insert 606, 607, 608, and 609 is configured to receive a weight to adjust the net density, center of gravity, and specific gravity of float 604. In one or more embodiments, each insert 606, 607, 608, and 609 is configured to receive a different weight having a different density to adjust the net density, center of gravity, and specific gravity of float 604. In some embodiments, where multiple floats 604 are placed in a rotatable component, such as rotatable component 308 of fluid flow control device 300, different weights 604 having different densities are inserted into one or more of inserts 606-609. In some embodiments, an impermeable exterior shell is formed around inserts 606-609 to prevent fluids from penetrating the shell. In some embodiments, the exterior shell is formed from a metal, a metallic alloy, polyether ether ketone, a plastic, or another material that is impermeable.

Figure 7:
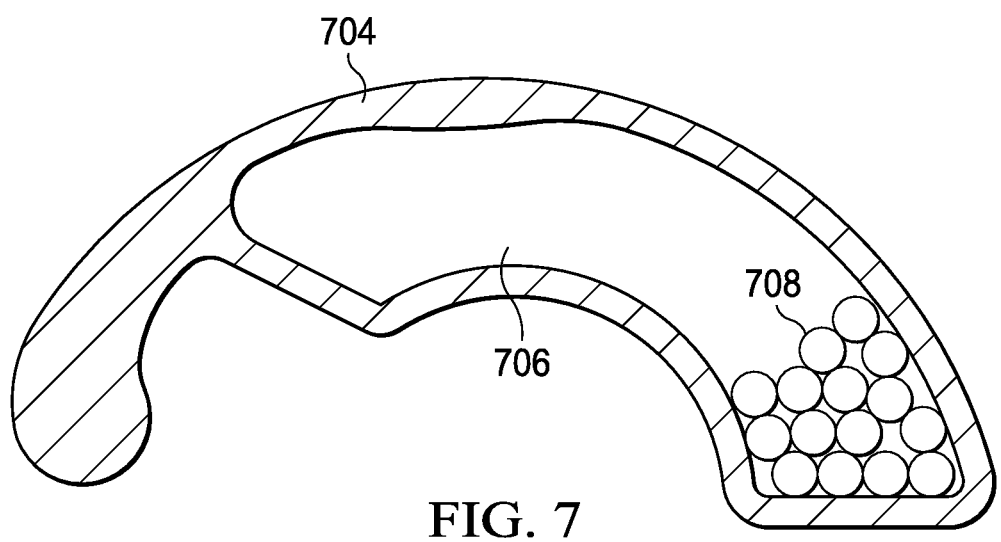
FIG. 7 is a cross-sectional view of another type of float of the fluid flow control device of FIG. 3.

FIG. 7 is a cross-sectional view of another type of float 704 of fluid flow control device 300 of FIG. 3. In the embodiment of FIG. 7, a cavity 706 that is partially filled with one or more weights 708 is formed inside float 704. Further, weights 708 are shiftable inside cavity 706, such as from the positions illustrated in FIG. 7 towards the opposite end of cavity 706. In some embodiments, float 704 shifts from an open position to a closed position as weights 708 shift from the position illustrated in FIG. 7 to another position, such as to the opposite end of cavity 706. In some embodiments, the center of mass of float 704 shifts as weights 708 shift from one position to another position. In some embodiments, an impermeable exterior shell is formed around cavity 706 to prevent fluids from penetrating the shell. In some embodiments, the exterior shell is formed from a metal, a metallic alloy, polyether ether ketone, a plastic, a thermoplastic, an epoxy, a composite or another material that is impermeable.

Figure 8A:
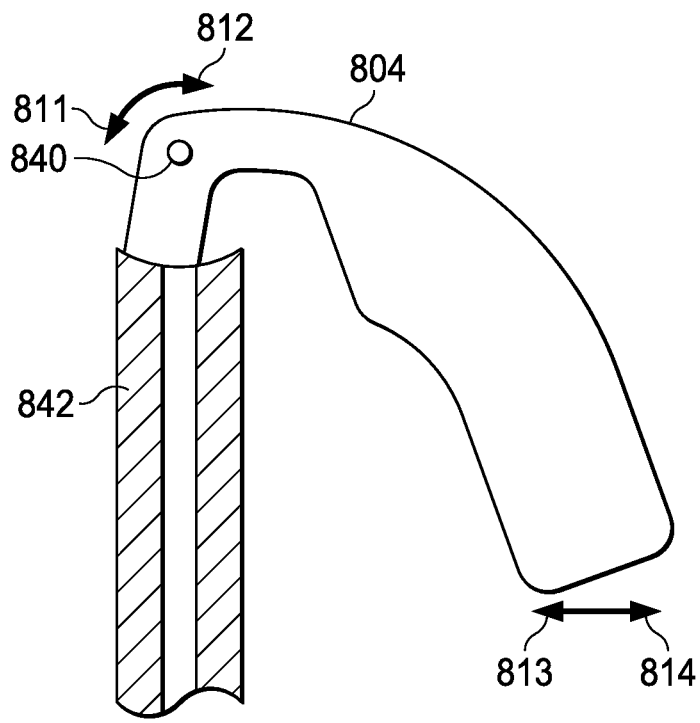
FIG. 8A is a perceptive view of another float of the fluid flow control device of FIG. 3 while the float is in a first position.

FIG. 8A is a perceptive view of another float 804 of fluid flow control device 300 of FIG. 3 while the float 804 is in a first position illustrated in FIG. 8A. In the embodiment of FIG. 8A, float 804 is in a closed position that restricts fluid flow through fluid pathway 842, which is similar to fluid pathways 342A-342C of FIG. 3, fluidly connects inlet port 305 of FIG. 3 with outlet port 307 of FIG. 3. Float 804 is coupled to a hinge 840, which provides for movement of float 804 in directions illustrated by arrows 811 or 812 about hinge 840. In some embodiments, float 804 is coupled to hinge 840 such that float 804 slides off fluid pathway 842 as float shifts from the closed position to the open position to reduce the threshold amount of force required to shift the float from the closed position to the open position.

Figure 8B:
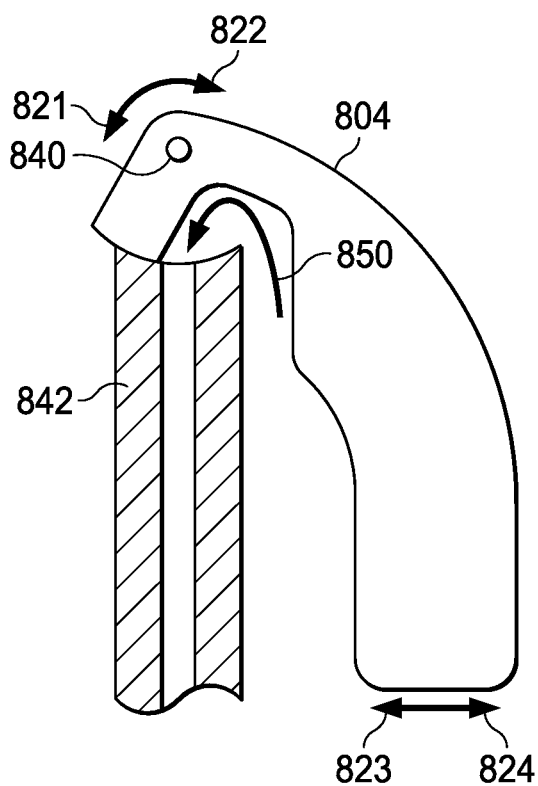
FIG. 8B is a perspective view of the float of FIG. 8A after the float has shifted to a second position to provide fluid communication to an outlet port of the fluid flow control device.

FIG. 8B is a perspective view of float 804 of FIG. 8A after float 804 has shifted to a second position to provide fluid communication to an outlet port of fluid flow control device 300 as shown in FIG. 3. In the embodiment of FIG. 8B, force from a fluid having a density that is less than the threshold density of float 804 moved float 804 about hinge 840 from the position illustrated in FIG. 8A to the position illustrated in FIG. 8B. Further, float 804 has also circumferentially shifted around fluid pathway 842 from the position illustrated in FIG. 8A to the position illustrated in 8B, which shifts float 804 to an open position as illustrated in FIG. 8B. While float 804 is in the open position, fluids flow into fluid pathway 842 (such as, for example, in a direction illustrated by arrow 850) and eventually to an outlet port such as outlet port 307 of FIG. 3.

Figure 9:
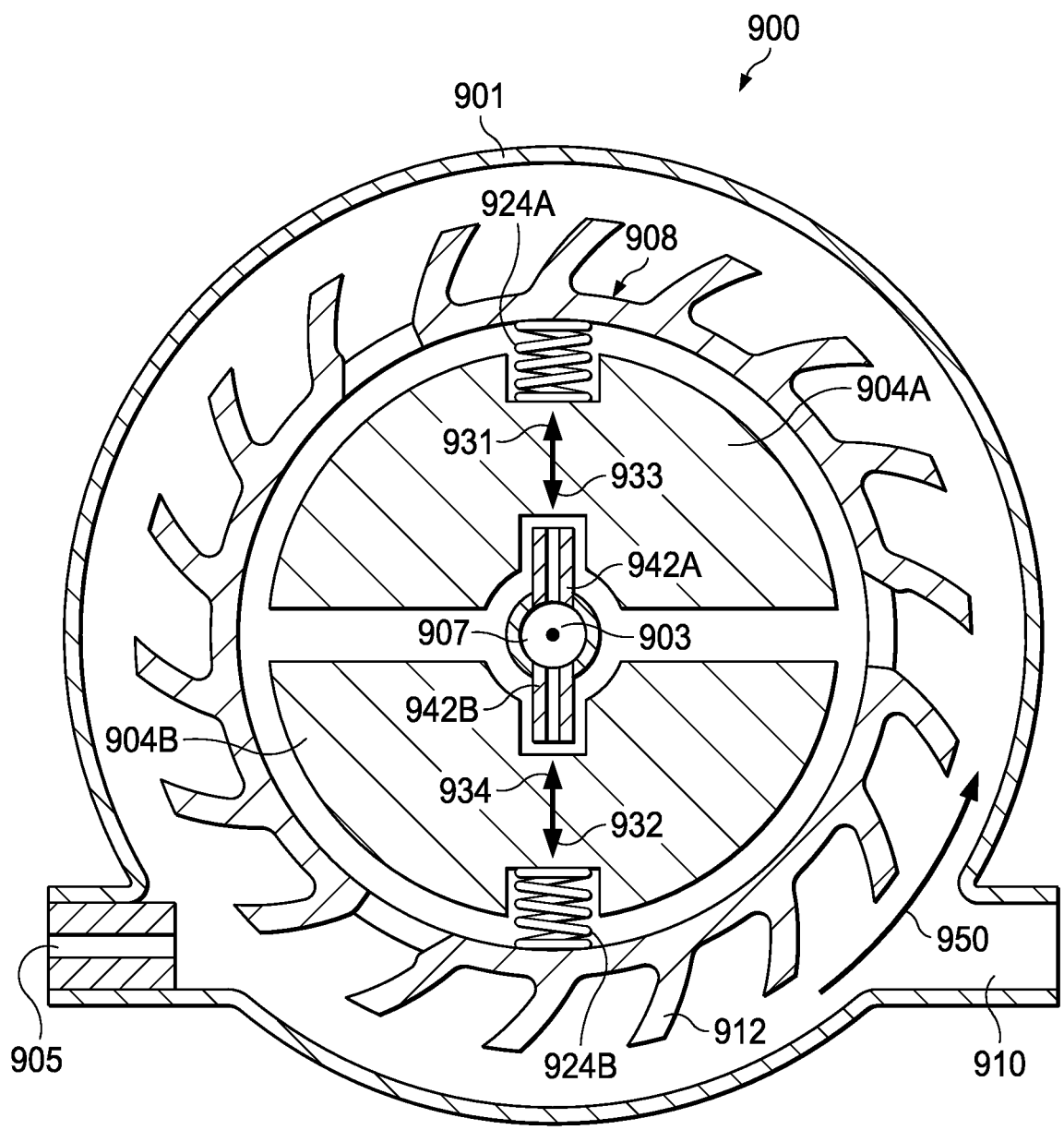
FIG. 9 is a cross-sectional view of another fluid flow control device deployable in the embodiment of FIG. 1.

FIG. 9 is a cross-sectional view of another fluid flow control device 900 that is deployable in the embodiment of FIG. 1. With reference now to FIG. 9, fluid flow control device 900 includes a rotatable component 908 positioned within a housing 901 of fluid flow control device 900. Fluid flow control device 900 also includes an inlet port 905 that provides a fluid passage for fluids, such as but not limited to, hydrocarbon resources, wellbore fluids, water, and other types of fluids to flow into housing 901. Fluid control device 900 also includes an outlet port 910 that provides a fluid flow path for fluids to flow out of fluid flow control device 900, such as to vortex valve 220 of FIG. 2. Some of the fluids that flow into housing 901 also come into contact with rotatable component 908, where force generated by fluids flowing onto rotatable component 908 rotates rotatable component 908 about axis 903. In some embodiments, fluids flowing through inlet port 905 push against fins, including fin 912, which are coupled to rotatable component 908. Moreover, the force of the fluids against the fins rotate rotatable component 908 about axis 903. Two floats 904A and 904B are positioned within the rotatable component 908, and are configured to permit or restrict fluid flow through fluid pathways 942A and 942B, respectively, which are fluidly connected to outlet port 907. In the embodiment of FIG. 9, floats 904A and 904B are partially filled with a foam material that has a density that is less than a threshold density (e.g., less than the density of water). In some embodiments, floats 904A and 904B are partially filled with weights, cavities, inserts, and other components described herein and illustrated in FIGS. 4-7. Two springs 924A and 924B are also positioned near or are coupled to floats 904A and 904B. As fluids flow into inlet port 905, force of the fluids flowing onto the fins of rotatable component 908 rotates rotatable component 908 in a direction illustrated by arrow 950. Moreover, a centrifugal force generated by an increase in the velocity of rotatable component 908 radially shifts floats 904A and 904B outwards in directions illustrated by arrows 931 and 932, respectively, and away from fluid pathways 942A and 942B, respectively, thereby allowing fluids to flow through fluid pathways 942A and 942B and into outlet port 907. Floats 904A and 904B also press against springs 924A and 924B, respectively, thereby compressing springs 924A and 924B. Over time, as the velocity and/or acceleration of rotatable component 908 decreases, the force of compressed springs 924A and 924B onto float 904A and 904B supersedes the centrifugal force generated by rotation of rotatable component 908, and shifts floats 904A and 904B radially inwards in directions illustrated by arrows 933 and 934, respectively, and towards fluid pathways 942A and 942B, respectively, thereby restricting fluids from flowing through fluid pathways 942A and 942B and into outlet port 907.

Although FIG. 9 illustrates two floats 904A and 904B, in some embodiments, a different number of floats are placed in rotatable component 908. Further, Although FIG. 9 illustrates two springs 924A and 924B, in some embodiments, a different number of springs are placed at different locations in rotatable component 908. In some embodiments, inlet port 905 is placed at a different location such that fluids flowing through inlet port 905 rotate rotatable component 908 in a direction opposite the direction illustrated by arrow 950.

The above-disclosed embodiments have been presented for purposes of illustration and to enable one of ordinary skill in the art to practice the disclosure, but the disclosure is not intended to be exhaustive or limited to the forms disclosed. Many insubstantial modifications and variations will be apparent to those of ordinary skill in the art without departing from the scope and spirit of the disclosure. For instance, although the flowcharts depict a serial process, some of the steps/processes may be performed in parallel or out of sequence, or combined into a single step/process. The scope of the claims is intended to broadly cover the disclosed embodiments and any such modification. Further, the following clauses represent additional embodiments of the disclosure and should be considered within the scope of the disclosure.

Clause 1, a fluid flow control device, comprising: a port; a rotatable component that rotates about an axis in response to fluid flow from the port; an outlet port that provides a fluid passageway out of the rotatable component; and a float positioned within the rotatable component, wherein the float is shiftable from an open position to a closed position, and wherein the float restricts fluid flow through the outlet port while the float is in the closed position.

Clause 2, the fluid flow control device of clause 1, wherein the float comprises a cavity disposed within the float.

Clause 3, the fluid flow control device of clause 2, wherein the cavity is partially filled with a material having a density such that the float and the material have a net density that is above a first density of a desired fluid and is below a second density of an undesired fluid.

Clause 4, fluid flow control device of clauses 2 or 3, wherein the float comprises a weight disposed within the cavity, and wherein the weight is movable within the cavity.

Clause 5, the fluid flow control device of clause 4, wherein the weight is movable from a first position to a second position inside the cavity, wherein the float shifts from the open position to the closed position as the weight moves from the first position to the second position, and wherein the float shifts from the closed position to the open position as the weight moves from the second position to the first position.

Clause 6, the fluid flow control device of any of clauses 1-5, wherein the float comprises a foam disposed within the float and having a density such that the float and the foam have a net density that is above a first density of a desired fluid and is below a second density of an undesired fluid.

Clause 7, the fluid flow control device of any of clauses 1-6, wherein the float comprises an insert formed along a portion of the float and configured to receive a weight.

Clause 8, the fluid flow control device of clause 7, wherein the float comprises a second insert formed along a second portion of the float and configured to receive a second weight, wherein the weight has a density that is different from the second weight.

Clause 9, the fluid flow control device of any of clauses 1-8, further comprising a spring, wherein the float compresses the spring as the float shifts radially outward towards a parameter of the rotatable component, and wherein the spring shifts the float towards the outlet port as the spring returns to a natural state.

Clause 10, the fluid flow control device of clause 9, wherein the float compresses the spring as the float shifts from the closed position to the open position, and wherein the spring shifts the float from the open position to the closed position as the spring returns to the natural state.

Clause 11, the fluid flow control device of any of clauses 1-10, wherein the float shifts circumferentially around the outlet port as the float shifts from the open position to the closed position.

Clause 12, a downhole float, comprising: an impermeable exterior; and a cavity formed within the float, wherein the float is disposed within a rotatable component that is deployable in a downhole environment, and wherein the float is shiftable from an open position to a closed position to restrict fluid flow out of an outlet port of the rotatable component.

Clause 13, the downhole float of clause 12, wherein the cavity is partially filled with a material having a density such that the float and the material have a net density that is above a first density of a desired fluid and is below a second density of an undesired fluid.

Clause 14, the downhole float of clause 13, wherein the float comprises a weight disposed within the cavity, and wherein the weight is movable within the cavity.

Clause 15, the downhole float of clause 14, wherein the weight is movable from a first position to a second position inside the cavity, wherein the float shifts from the open position to the closed position as the weight moves from the first position to the second position, and wherein the float shifts from the closed position to the open position as the weight moves from the second position to the first position.

Clause 16, the downhole float of any of clauses 12-15, wherein the float comprises a foam disposed within the float and having a density such that the float and the foam have a net density that is above a first density of a desired fluid and is below a second density of an undesired fluid.

Clause 17, the downhole float of any of clauses 12-16, wherein the float shifts radially outwards towards a parameter of the rotatable component as the float shifts from the closed position to the open position.

Clause 18, the downhole float of any of clauses 12-17, wherein the float shifts circumferentially around a point on the rotatable component as the float shifts from the open position to the closed position.

Clause 19, a downhole float, comprising: an impermeable exterior; and an insert formed along a portion of the float and configured to receive a weight, wherein the float is disposed within a rotatable component that is deployable in a downhole environment, and wherein the float is shiftable from an open position to a closed position to restrict fluid flow out of an outlet port of the rotatable component.

Clause 20, the downhole float of clause 19, wherein the float comprises a second insert formed along a second portion of the float and configured to receive a second weight, wherein the weight has a density that is different from the second weight.

As used herein, the singular forms "a," "an," and "the" are intended to include the plural forms as well, unless the context clearly indicates otherwise. It will be further understood that the terms "comprise" and/or "comprising," when used in this specification and/or in the claims, specify the presence of stated features, steps, operations, elements, and/or components, but do not preclude the presence or addition of one or more other features, steps, operations, elements, components, and/or groups thereof. In addition, the steps and components described in the above embodiments and figures are merely illustrative and do not imply that any particular step or component is a requirement of a claimed embodiment.

What is claimed is:

1. A fluid flow control device, comprising:
   a port;
   a rotatable component that rotates about an axis in response to fluid flow from the port;
   an outlet port that provides a fluid passageway out of the rotatable component; and
   a float positioned within the rotatable component, wherein the float is shiftable from an open position to a closed position, and wherein the float restricts fluid flow through the outlet port while the float is in the closed position,
   wherein the float comprises at least one of:
   1) A cavity disposed in the float and having a boundary that is entirely within a boundary of the float;
   2) an insert formed along a portion of the float and configured to receive a weight, and a second insert formed along a second portion of the float and configured to receive a second weight, wherein the weight has a density that is different from the second weight; and
   3) a spring, wherein the float compresses the spring as the float shifts radially outward towards a parameter of the rotatable component, and wherein the spring shifts the float towards the outlet port as the spring returns to a natural state.

2. The fluid flow control device of claim 1, wherein the cavity is partially filled with a material such that the float and the material have a net density that is above a first density of a desired fluid and is below a second density of an undesired fluid.

3. The fluid flow control device of claim 1, wherein the float comprises a weight disposed within the cavity, and wherein the weight is movable within the cavity.

4. The fluid flow control device of claim 3, wherein the weight is movable from a first position to a second position inside the cavity, wherein the float shifts from the open position to the closed position as the weight moves from the first position to the second position, and wherein the float shifts from the closed position to the open position as the weight moves from the second position to the first position.

5. The fluid flow control device of claim 1, wherein the float comprises a foam disposed within the float and having a density such that the float and the foam have a net density that is above a first density of a desired fluid and is below a second density of an undesired fluid.

6. The fluid flow control device of claim 1, wherein the float compresses the spring as the float shifts from the closed position to the open position, and wherein the spring shifts the float from the open position to the closed position as the spring returns to the natural state.

7. The fluid flow control device of claim 1, wherein the float shifts circumferentially around the outlet port as the float shifts from the open position to the closed position.

8. A downhole float, comprising:
   an impermeable exterior; and
   a cavity formed within the float and having a boundary that is entirely within a boundary of the float, wherein the float is disposed within a rotatable component that is deployable in a downhole environment, and
   wherein the float is shiftable from an open position to a closed position to restrict fluid flow out of an outlet port of the rotatable component.

9. The downhole float of claim 8, wherein the cavity is partially filled with a material having a density such that the float and the material have a net density that is above a first density of a desired fluid and is below a second density of an undesired fluid.

10. The downhole float of claim 9, wherein the float comprises a weight disposed within the cavity, and wherein the weight is movable within the cavity.

11. The downhole float of claim 10, wherein the weight is movable from a first position to a second position inside the cavity, wherein the float shifts from the open position to the closed position as the weight moves from the first position to the second position, and wherein the float shifts from the closed position to the open position as the weight moves from the second position to the first position.

12. The downhole float of claim 8, wherein the float comprises a foam disposed within the float and having a density such that the float and the foam have a net density that is above a first density of a desired fluid and is below a second density of an undesired fluid.

13. The downhole float of claim 8, wherein the float shifts radially outwards towards a parameter of the rotatable component as the float shifts from the closed position to the open position.

14. The downhole float of claim 8, wherein the float shifts circumferentially around a point on the rotatable component as the float shifts from the open position to the closed position.

15. A downhole float, comprising:
an impermeable exterior; and
an insert formed along a portion of the float and configured to receive a weight, and a second insert formed along a second portion of the float and configured to receive a second weight, wherein the weight has a density that is different from the second weight,
wherein the float is disposed within a rotatable component that is deployable in a downhole environment, and
wherein the float is shiftable from an open position to a closed position to restrict fluid flow out of an outlet port of the rotatable component.

\* \* \* \* \*